United States Patent [19]

Ferrara et al.

[11] Patent Number: 5,129,033

[45] Date of Patent: Jul. 7, 1992

[54] DISPOSABLE THERMOSTATICALLY CONTROLLED ELECTRIC SURGICAL-MEDICAL IRRIGATION AND LAVAGE LIQUID WARMING BOWL AND METHOD OF USE

[76] Inventors: Janice J. Ferrara, 11605 Timberly Waye, Richmond, Va. 23233; Peter Bauer, 13921 Esworthy Rd., Germantown, Md. 20874

[21] Appl. No.: 496,256

[22] Filed: Mar. 20, 1990

[51] Int. Cl.[5] .............. H05B 1/02; A61J 1/00; A47J 27/62; F24H 1/06
[52] U.S. Cl. .................. 392/447; 219/436; 219/437; 219/438; 219/441; 219/443; 219/510; 392/498; 392/503
[58] Field of Search ............. 219/436–438, 219/441–443, 432, 433, 510; 392/444–447, 498, 503

[56] References Cited

U.S. PATENT DOCUMENTS

| 1,158,488 | 11/1915 | Hadaway et al. | 219/437 X |
|---|---|---|---|
| 1,464,255 | 8/1923 | Zimmerman | 219/436 X |
| 2,134,675 | 10/1938 | Shroyer | 392/447 X |
| 2,258,210 | 10/1941 | Maxwell | 219/436 |
| 2,817,744 | 12/1957 | Free | 219/439 |
| 2,892,066 | 6/1959 | Springer | 219/435 |
| 2,994,761 | 8/1961 | Hart et al. | 219/443 X |
| 3,038,058 | 6/1962 | Gordon | 219/441 X |
| 3,290,484 | 12/1966 | Day | 219/441 |
| 3,678,246 | 7/1972 | Blachly et al. | 219/437 |
| 3,931,494 | 1/1976 | Fisher et al. | 219/441 |
| 3,973,102 | 8/1976 | Macklem | 219/442 X |
| 4,956,544 | 11/1990 | Sayward | 219/437 X |
| 4,967,061 | 10/1990 | Weber et al. | 219/438 |

FOREIGN PATENT DOCUMENTS

| 806721 | 6/1951 | Fed. Rep. of Germany | 219/442 |
|---|---|---|---|
| 593638 | 5/1925 | France | 219/442 |
| 410169 | 5/1934 | United Kingdom | 219/205 |

*Primary Examiner*—Anthony Bartis

[57] ABSTRACT

A warming bowl for electrically heating lavage and irrigation liquid for use during medical-surgical procedures includes an electric heating device and an automatic thermostatic control to heat and maintain the liquid at a substantially constant temperature. The warming bowl is disposable after use and has an inner and an outer bowl sealed to one another so as to provide an internal sealed region therebetween for holding a battery to power the electric heating device. The inner bowl serves to hold irrigation liquid and supports therein a housing made of low-thermal-conductivity material that houses the electric heating device and the thermostatic control in spaced, substantially thermally isolated relation from one another. A metallic thermal shunt conductor is disposed along and in contact with a portion of the external periphery of the housing and extends over and across the space between the heating device and the thermostatic control. The housing is fixedly supported spacedly above the inner bowl's bottom. When the inner bowl is filled with irrigation liquid, a major portion of the housing is exposed to the liquid at least over a substantial part of the outer surface of the shunt conductor. An external power source can be selectively optionally connected to power the heating device.

13 Claims, 2 Drawing Sheets

DISPOSABLE THERMOSTATICALLY CONTROLLED ELECTRIC SURGICAL-MEDICAL IRRIGATION AND LAVAGE LIQUID WARMING BOWL AND METHOD OF USE

BACKGROUND OF THE INVENTION

1. Field of the Invention

This invention relates to bowls for holding liquids for irrigation and lavage purposes employed during medical surgical procedures, particularly in hospital operating rooms, and it provides for heating of these liquids while in such bowls, for instance heating and maintaining the liquids substantially at body temperatures.

2. Prior Art and Other Considerations

In general, bowls holding liquids for irrigation and lavage purposes are utilized during most medical surgical procedures. These bowls are commonly located in close proximity of the operating table on a tray to be easily accessible by operating room personnel. When a need arises for irrigation, for instance of bodily tissues, usually syringes of the bulg or cylinder/piston type are used to aspirate liquid from the bowl and to eject the liquid onto the area required to be irrigated. For example, saline, antibiotic, and other irrigation and lavage solutions are generally applied in this manner. Sometimes also, for instance, lap sponges are used to soak up irrigation liquid from the bowl for transfer of the liquid to body areas.

It will be appreciated that the temperature of the irrigation liquids is desired to be substantially the same as the body temperature to avoid patient discomfort and thermal shock to irrigated body tissues. Customary operating room practice in the past has been to pre-warm the liquids to body temperature prior to filling and topping up of the bowls and to rely upon the relatively large heat capacity of such liquids to avoid significant temperature reductions. Whereas such practice may be adequately satisfactory during rather brief surgical procedures, extended surgery results in significant undesirable cooling of the liquids.

Consequently, repeated emptying and refilling of the bowls with appropriately pre-heated liquid has been required in the past. The liquid emptied from bowls is almost invariably considered non-reusable and is therefore wasted. Moreover, even repeated refilling does not assure that liquid temperatures are followed to assure continuous detection of incorrect temperatures. Furthermore, no provision has been made to assure that the temperature of the liquid use in filling and refilling of the bowls is correct. Consequently, temperatures of the irrigation liquids in bowls can be as low as the ambient room temperature or even lower in an extreme situation, when liquid is brought from cooler storage areas and is mistakenly used without preheating (and without monitoring). The temperature of the liquid can be also above body temperature, if temperature monitoring during preheating is absent or inadequate.

It has been recognized in related prior art that fluid for dispensing onto bodily tissues during medical procedures should be heated and maintained at a desired proper temperature. For instance, U.S. Pat. No. 1,837,932 issued to Weigle describes medical syringes in which contained fluid is constantly maintained at a desired temperature during continuous use of the syringe.

An example of heating and maintaining fluid in a container at constant body temperature for surgical use is shown in U.S. Pat. No. 4,180,722 issued to Clewans. Clewans discloses heating of fluid contained in a sterile bottle by an externally disposed infrared heated having automatic temperature control including photoelectric sensing of color of a liquid crystal temperature sensor disposed within the bottle.

An example of a fluid heating device for medical dental spray use is disclosed in U.S. Pat. No. 4,041,276, issued to Schwarz et al, wherein a semiconductor is employed as the heating element while also serving to regulate temperature.

Containers holding medical irrigation solutions specifically for filling of irrigation syringes therefrom are, for instance, disclosed in U.S. Pat. Nos. 3,380,489 (Harautuneian) and 4,175,597 (Peterson).

Despite a long-felt need, appropriately sutiable irrigation liquid heating bowls for medical irrigation and lavage purposes providing constant temperature liquid during surgical procedures and satisfactorily facilitating pick-up or aspiration of the liquid by a variety of surigical instruments have not been available.

Accordingly, an overall feature of the invention is the provision of a warming bowl for irrigation liquid to heat the liquid contained therein by automatic thermostatic control so that appropriate liquid temperatures are attained and maintained in the course of surgical procedures, and to facilitate pick-up or aspiration of irrigation liquid from the warming bowl by means of syringes, sponges, and the like for subsequent irrigation of lavage of bodily tissue.

SUMMARY OF THE INVENTION

In accordance with principles of the present invention, an irrigation liquid warming bowl is provided including an electric heating device and associated circuitry to heat the liquid to and maintain the liquid at a substantially constant temperature by automatic thermostatic control. A preferred embodiment of the invention includes a battery power source within the structure of the bowl.

In particular, the irrigation liquid warming bowl of the invention comprises a bowl assembly including an inner and as outer bowl sealed to one another. An internal sealed hollow region is provided between the inner and outer bowls, and the inner bowl forms a basin-shaped depression for holding irrigation liquid. A heater and a thermostat are disposed within a housing that is substantially fixedly supported in the inner bowl and that is spaced from the bottom of the inner bowl to permit liquid circulation and effective heat transfer along major portions of its surface. The heater and the thermostat are spaced from one another and have a thermally insulating region or cavity disposed therebetween. At least one battery is located in the internal sealed hollow region for powering of the heater. In one embodiment additionally an external power source can be selectively optionally connected to power the heater.

Thermostatic control means are provided that include the thermostatic and further include a thermal shunt conductor that is disposed on the outer surface of the housing and closely fitting thereover. The thermal shunt conductor extends between and substantially over the housing regions that contain the heater and the thermostat.

In use and operation of the irrigation liquid bowl of the invention, the heater heats liquid held in the inner bowl until the thermostat senses the preset cut-off temperature when the thermostat deactivates the heater. As the liquid temperature decreases below the threshold of the preset thermostat, the thermostat again activates the heater. More specifically, the heater provides heat through the housing wall and to the thermal shunt conductor and therefrom to the irrigation liquid. When the inner bowl contains adequate liquid, the liqiud (acting as a heat sink) dissipates and distributes heat so that the thermal shunt conductor substantially tracks the liquid temperature (the thermal shunt conductor temperature being sensed by the thermostate). The thermal shunt conductor provides a relatively fast shunt path for heat between the heater and the thermostat in absence of an adequate liquid heat sink (if inadequate liquid is present in the inne bowl) and results in a quick response of the thermostat to a consequent increased shunt conductor temperature and thereby effects deactivation of the heater.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference numerals refer to like parts throughout different views. The drawings are schematic and not necessarily to scale, emphasis instead being placed upon illustrating principles of the invention.

DESCRIPTION OF THE PREFERRED EMBODIMENTS

Figure 2:
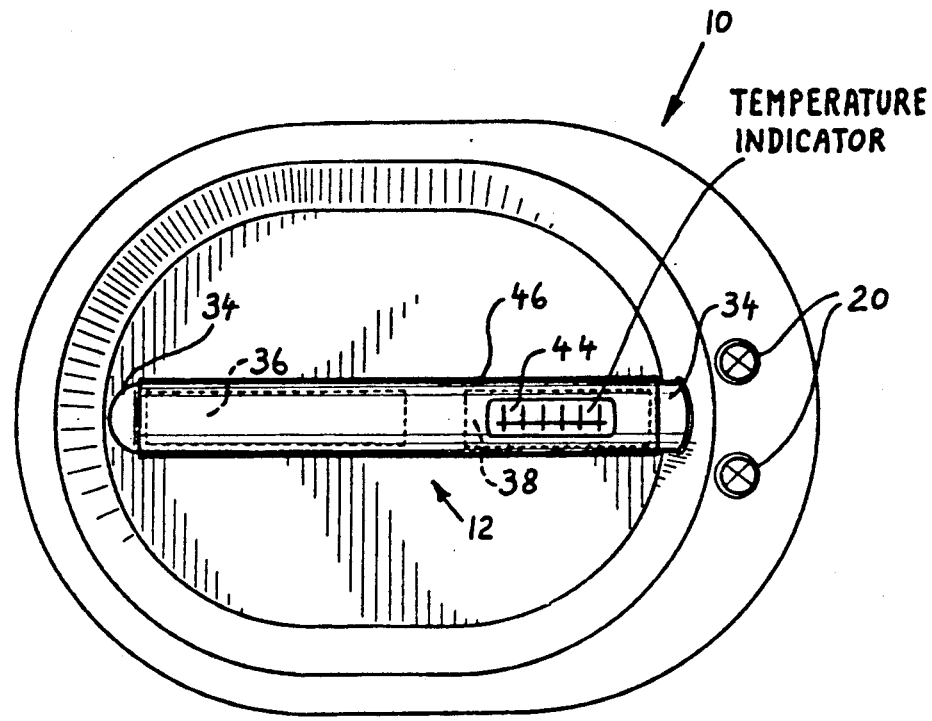
FIG. 2 is a schematic plan view of the embodiment shown in FIG. 1.
Figure 1:
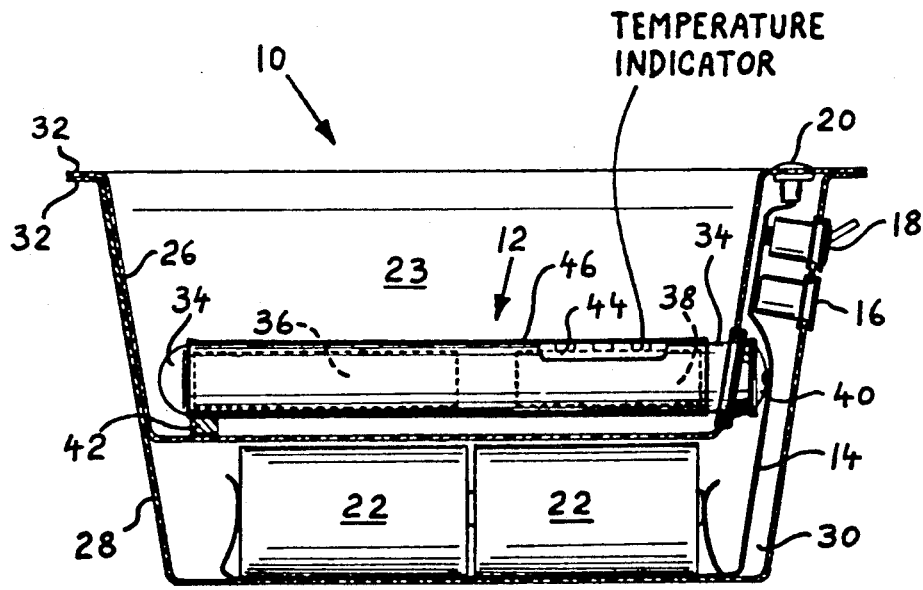
FIG. 1 is a schematic particial vertical section view of an embodiment of the present invention.

Referring now to FIGS. 1 and 2, an irrigation liquid warming bowl 10 is shown to include a heater device 12, circuitry wiring 14, an electrical plug receptacle 16 for external power connection, a switch 18 for selective actuation or energization of the heater device 12, and monitor lamps 20 for displaying operating status of the heater device 12. Bowl 10 is shown to further include batteries 22 for internal powering of heater device 12.

Bowl 10 has a double-wall construction, comprising an inner bowl 26 and an outer bowl 28 that are assembled with one another in a substantially leak-proof manner so that a sealed hollw region 30 is formed between the inner and outer bolws. Inner bowl 26 has a basin-shaped depression 23 that is upwardly open to ambient for holding the irrigation liquid. Inner bowl 26 and outer bowl 28 are provided along their rims with substantially horizontal flanges 32 which are of substantially similar sizes and shapes so that they present matching juxtaposed surfaces to one another. Bowls 21 and 28 are bonded to one another along these juxtaposed surfaces in order to provide structural rigidity of th assembly and sealing of the hollow region 30 with respect to ambient.

As depicted, bowls 26 and 28 have a generally oval shape with tapered side walls and a substantially flat bottom. Inner bowl 26 is shallower and has a shorter length than outer bowl 28, yet formfittingly nests within outer bowl 28 along its curved left side and along portions of the lateral walls, while being spaced from outer bowl 28 at the right side. Sizes and shapes of bowls 26 and 28 are preferably chosen to facilitate at least partial nesting of a number of assembled bowls 10 for storage and packing convenience. For instance bowl 10 can be nested with approximately a third of its height disposed in another like bowl 10, and a number of the bowls can be stacked in such a space-saving manner.

Heater device 12 comprises a housing 34 that is, for instance, of relatively high temperature plastic material such as a polysulfone polymer or of heat resistant glass or other heat resistant material in the general shape of a test tube. Housing 34 includes hermetically sealed therein a heater 36 and a thermostat 38 (schematically indicated by dashed lines). Heater 36 and thermostat 38 are spaced from one another to avoid a direct heat transfer path therebetween within housing 34. The right hand end opening of housing 34 is provided with a hermetically sealing plug 40 that provides for entry of wire conductors for feedthrough of electrical power. These conductors connect circuitry wiring 14 in hollow region 30 with heater 36 and thermostat 38.

Housing 34 is mounted and sealed in a mating hole in the right hand side wall of inner bowl 26. A support block 42 is provide to assist in supporting the left hand end of housing 34 upon the bottom surface of inner bowl 26. Housing 34 is thusly oriented substantially horizontally and is spaced from the bottom of inner bowl 26 by a small distance to permit liquid circulation and effective heat transfer along major portions of its surface.

A temperature indicator 44 is preferably disposed on the upper portion of housing 34 to be visible from above bowl 10 and to indicate the temperature of the liquid contained therein. For example, temperature indicator 44 can be of a liquid crystal type, as commercially available in form of flexible self-adhesive pads. The temperature indicator can be disposed alternately along an inner or outer side wall or in another suitable location, and it can be any other conventional kind of thermometric device to provide visual temperature indication of the contents of bowl 10.

Electrical plug receptacle 16, switch 18, and monitor lamps 20 are sealedly mounted in top and/or walls of bowl 10 so that hollow region 30 remains hermetically sealed with respect to ambient. Electrical plug receptacle 16, switch 18, and monitor lamps are connected to circuitry wiring 14. Batteries 22 are permanently pasituned in hollow region 30 in the bottom portion of outer bowl 28, and they are appropriately connected to circuitry wiring 14. Batteries are indicated in form and size corresponding to commercially available 'D size cells and are preferably of a high capacity alkaline type. Lithium type batteris are a preferred alternative. Batteries having an external shape conforming to the shape of the bottom cavity between outer and inner bowls 26 and 28 are naturally preferred.

In use of bowl 10 during surgical procedures, bowl 10 or more specifically much of the volume in inner bowl 26 is filled with irrigation liquid and switch 18 is switched on to activate the automatic heating process.

Switch 18 connects the electrical power provided by batteris 22 to heater 36 via thermostat 38. Thermostat 38 interrupts the current fed to heater 36 when the thermostatically preset temperature is reached, and reestablishes the current path when the tempertaure decreases below the threshold of the preset thermostat. This automatic thermostatic control continues on/off cycling of the heater power as long as switch 18 remains turned on. Monitor lamps 20 visually indicate the status of switch 18 and the availability of electrical power and further can visually indicate the cycling of the heater current. Temperature indicator 44 facilitates continuous monitoring of temperature even if electrical power is not switched on or is otherwise unavailable.

Monitoring lamps 20 are preferably of the light emitting diode type, but can be of any other conventional visible light emitting kind.

It will be appreciated the thermostat 38 is also operative in the manner of a safety device to prevent overheating of and by the heater 36 in absence of adequate liquid depth in basin-shaped depression 23, if switch 18 is inadvertently switched on under such circumstances. For instance, if no liquid is disposed in basin-shaped depression 23 or if liquid therein does not cover at least a substantial portion of housing 34, the temperature sensed by thermostat 38 will be briefly below its preset cut-off threshold. In this situation, thermostat 38 energizes and quickly thereafter disconnects heater 36, as the temperature in the region of the heater and the thermostat increases relatively rapidly above the preset threshold due to the absence of an adequate liquid heat sink for housing 3j. Consequently overheating is thereby safely prevented. Monitor lamps 20 also provide a visual display of such a situation. The monitor lamp indicating status of switch 18 will be lit and the monitor lamp indicating thermostat cycling will flash repetitively with short duration flashes or relatively rapid repetition rate; the latter particularly indicating this situation of inadequate liquid depth or of the absence of liquid.

Figure 2A:
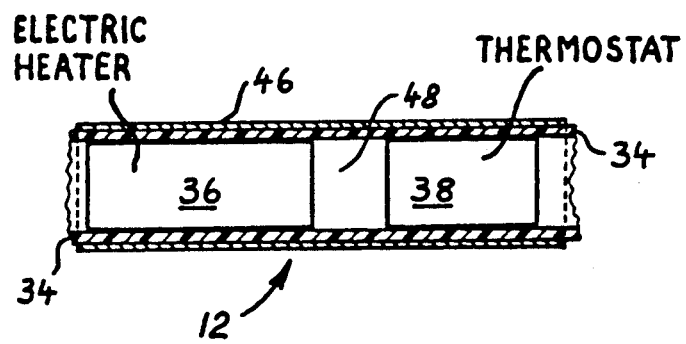
FIG. 2A is a schematic partial section depiction of a fragmental portion of the heater device shown in FIG. 1.

Provision can be made to further enhance the function of the above described safety feature by disposing, within housing 34, thermostate 38 spaced apart and thermally insulated from heater 36, and to provide on the external periphery of housing 34 a thermally conducting path between the vicinity of heater 36 and the vicinity of thermostat 38, as indicated in further detail in FIG. 2A.

Referring now to FIG. 2A, the shown fragmental sectional view of a portion of heater device 12, including heater 36 and thermostat 38 sealed within housing 34, further shows a thermal conductor 46 and an insulating region 48. Insulating region 48 is a cavity between heater 36 and thermostat 38 which is operative in thermally insulating the heater and the thermostat from one another. For instance, the cavity can contain air or another gas or it can be filled with thermally insulating material; for example glass wool or a similar material. Thermal conductor 46 is provided in form of a sleeve that is closely fitted to the outer surface of housing 34 and that extends between and substantially over the regions containing heater 36 and thermostate 38. Thermal conductor 46 need not entirely cover housing 34, as long as it is capable of providing an adequate thermal conduction path from the vicinity of the heater 36 to the vicinity of the temperature sensing portion of the thermostat 38. Thermal conductor 46 can be provided in form of a metal sleeve or a metal bar, in form of a metal plating upon the surface of housing 34, or in form of other thermally conductive overlays.

The function of thermal conductor 46 is to provide a relatively fast shunt path for heat between heater 36 and thermostat 38, so that overheating of the heater is prevented by quick response of the thermostat to an increased temperature in absence of an adequate liquid heat sink, as described in the foregoingl. When bowl 10 contains adequate liquid, the liquid dissipates and distributes heat so that thermal conductor 46 substantially tracks the liquid temperature. Consequently, normal thermostatic control cycling and heating of irrigation liquid results, as also described hereinbefore.

Although not considered essential, a thermal cut-off can be disposed proximatelly to heater 36 with a manually actuatable reset means disposed, for instance, in an external wall of outer bowl 28.

Electrical plug receptacle 16 serves to connect an appropriate external electrical power source to circuitry wiring 14 of bowl 10. Plug receptacle 16 is of a conventional jack type receptacle which, while connecting to an external power source, disconnects the internal battery power source from circuitry wiring 14 and replaces it by the external power source. Plug receptacle 16 is preferably of the type that provides this function in the conventionally often employed manner of "break before make".

Figure 3:
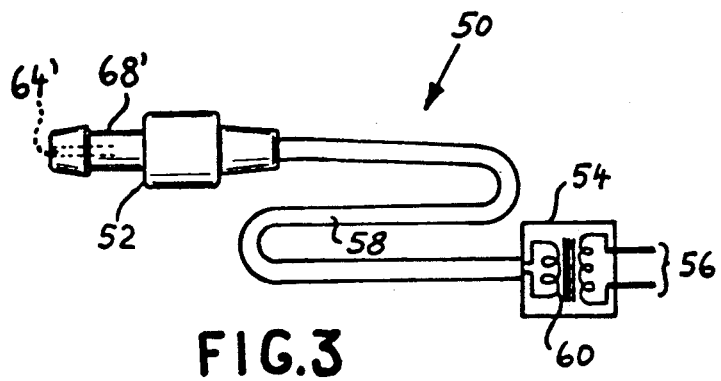
FIG. 3 is a schematic illustration of the an electric power connection device, according to an embodiment of the invention, for use with the device shown in FIG. 1.

Referring now to FIG. 3, an electric power connection device 50 is schematically shown that is suitable for connecting a normal high voltage alternating current building supply in appropriately transformed form to plug receptacle 16 of bowl 10. The heater system of bowl 10 can be thusly optionally selectively powered from an external electrical power source instead of from the internal batteries 22 at the operator's choice.

Electric power connection device 50 comprises a jack 52 for plugging into the plug receptable 16 (of FIG. 1), a transformer unit 54 having a supply plug unit or connector 56 for connecting to a room electrical supply outlet, and an electrical cord 58 interconnecting transformer unit 54 with jack 52. Transformer unit 54 comprises an isolation transformer 60 for reducing the rooom electrical supply voltage to a suitable lower voltage that is compatible with the requirements of heater device 12 (for instance a substantially similar voltage as provided by batteries 22), that is isolated from the room supply, and that is low enough to avoid dangers of accidental exposure to electrical shock. Transformer unit 54 can additionally include rectifying circuitry to provide direct current.

Irrigation liquid warming bowl 10 can employ either its internal power supply in form of the batteries 22 for heating of the liquid or, optionally, it can utilize an external supply provided by connection of bowl 10 to a suitable room electrical supply via electric power connection device 50. As a matter of convenience in use of the bowl 10 and in order to reduce capacity requirements for batteries 22, it can be advantageous to employ an external supply for heating of irrigation liquid in bowl 10 to body temperature, for example from room or a lower storage temperature, and thereafter employ only the bowl's internal battery power to maintain the desired liquid temperature. It will be appreciated that maintaining temperature demands much less power than raising it. A key feature of the use of internal battery power in the course of surgical procedures is the absence of cords trailing from bowls and the self-sufficiency of operation of the warming bowl device.

Customary procedure in the use of conventional (non-heating) irrigation liquid bowls has been to fill such plain bowls with irrigation liquid that has been preheated to body temperature in different containers in warming cabinets and the like prior to the start of surgical activities. Such conventional preparatory procedures can be followed in filling of the irrigation liquid warming bowls 10 of the present invention, yet thereafter bowls 10 can automatically maintain the desired temperature either under internal battery power or under external power supply, as discussed hereinbefore.

Nonetheless, the irrigation liquid warming bowl of the present invention can be employed directly to also automatically preheat the liquid as also described in the foregoing, either under internal battery power (provided that adequate battery capacity is included) or under external power supply.

The following descriptions are presented to further clarify customary conditions under which conventional irrigation liquid bowls are employed and, also in this context, to explain the need for the advantages provided by the characteristics of the bowl according to the present invention.

Irrigation liquid bowls are provided in pre-packaged pre-sterilized form ready for use, and they are non-reusable and disposable, in view of the strigent demands on aseptic conditions and also because of the high cost of reliable sterilization for reusable surgical instruments and accessories. In view of the critical nature of operating procedures and, therefore, the desirability to reduce cluttering in the vicinity of the operating table with accessory devices, particulary parts presenting possibilities for entanglement and of endangering aseptic conditions are best avoided, if at all possible. Consequently, for instance, power cords for heating of trays, bowls, etc. are, on the whole, undesirable in such locations.

Irrigation liquid has to be readily available for the duration of surigical procedures. It is considered that a two to two and one half hour availability of warmed irrigation liquid from a bowl represents a reasonable practical desideratum for a large number of surgical procedures. Consequently, batteries 22 need to be sized to have an adequate energy capacity to at least maintain the irrigation liquid in a filled bowl at body temperature for such a length of time.

Figure 4:
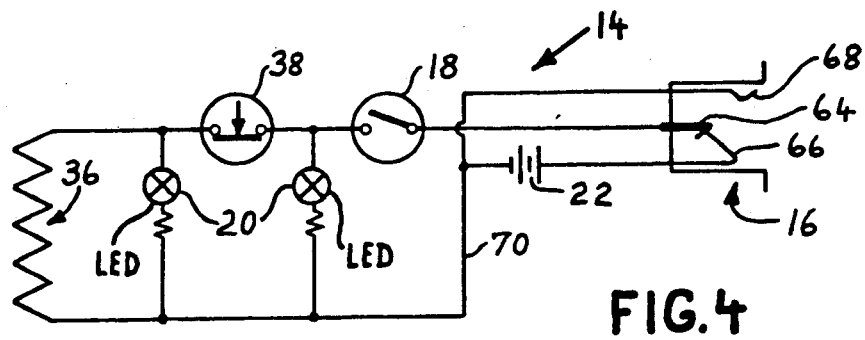
FIG. 4 is a schematic diagram of an electrical circuit, according to the inventio, for use in the device shown in FIG. 1.

Referring now to FIG. 4, the depicted circuit diagram shows interconnections between electrical components comprised in bowl 10 of FIGS. 1 and 2. Heater 36 is connected via thermostat 38 and switch 18 to battery 22, the circuit being closed through the contact arrangement in plug receptacle 16. One of the monitor lamps 20 is directly shunted across heater 36 and the other one is shunted across the series connection of heater 36 and thermostat 38. Monitor lamps 20 as shown as light emitting diodes including a current limiting resistor in series connection thereto. Heater 36 is a conventional resistance heater. Plug receptacle 16 comprises a main contact 64 leading to switch 18, a battery contact 66 directly connected to battery 22, and an external supply contact 68 leading to a common line 70. As shown, main contact 64 and battery contact 66 contact one another within plug receptacle 16, thereby closing the circuit of power being supplied by battery 22.

In operation, after switch 18 is closed, the right hand monitor lamp 20 lights up to indicate 'on' status. The left hand monitor lamp 20 is only on while thermostat 38 enables heater 36 to receive current. Consequently the latter lamp cycles on and off in correspondence with the operation of thermostat 38.

As an external power connection device, for example through jack 52 of the device 50 of FIG. 3, is plugged into plug receptacle 16, main contact 64 and battery contact 66 are separated and disconnected from one another first, thusly disabling battery 22 from providing power to the circuit. Subsequently, connection is made between main contact 64 and one (center) conductor 64 of the jack 52 and between external supply contact 68 and the other conductor 68 of the jack 52. Consequently, the battery power supply 22, that has been disconnected from the circuit, is replaced in the circuit by an external power supply feeding through jack 52. Unplugging of jack 52 reverses the connection process in plug receptacle 16 and again replaces battery 22 in the circuit.

While the invention has been particularly shown and described with reference to preferred embodiments thereof, it will be understood by those skilled in the art that various changes and modifications in form and details may be made therein without departing from the spirit and scope of the invention.

The embodiments of the invention in which an exclusive property or privilege is claimed are defined as follows:

1. An irrigation liquid warming bowl for holding and heating of liquid for irrigation and lavage purposes in medical surgical procedures, said irrigation liquid warming bowl being non-reusuably disposable, comprising:

a bowl assembly including an inner bowl and an outer bowl, said inner bowl serving to hold irrigation liquid and including a bottom, said outer bowl providing support for said inner bowl, said bowl assembly including an internal region defined between said inner and outer bowls, said internal region being liquid-tightly sealed with respect to ambient and with respect to liquid held in said inner bowl;

heating means for heating of irrigation liquid held in said inner bowl, said heating means including an electric heater and thermostatic control means and a housing made of a non-metallic low-thermal-conductivity material, said housing being fixedly supported substantially horizontally within said inner bowl spacedly from said bottom, said thermostatic control means serving for automatic control of said heater, said thermostatic control means including a thermostat, said thermostat and said heater being disposed within said housing in spaced substantially thermally isolated relationship from one another, said thermostatic control means including a thermal shunt conductor disposed along and in contact with at least a portion of the external periphery of said housing and extending over and across the space between said heater and said thermostat, said thermal shunt conductor extending substantially over and about the vicinal area of said heater and substantially over and about the vicinal area of said thermostat so that said thermostat is thereby exposed to and senses substantially primarily the temperature of said thermal shunt conductor;

power supply means for providing electrical power to said heating means, said power supply means including at least one battery disposed in said internal region;

on/off switching means for selective manual actuation and deactivation, respectively, of said power supply means;

status monitoring means for visual display of operating status of said power supply means and said heating means; and electrical circuitry for operatively interconnecting said heating means, said thermostatic control means, said on/off switching means, said status monitoring means, and said pwoer supply means.

2. The irrigation liquid warming bowl according to claim 1, including thermometric indicator means for indication and display of the temperature of irrigation liquid held in said inner bowl.

3. The irrigation liquid warming bowl of claim 1, wherein said status monitoring means includes at least one light emitting device.

4. The irrigation liquid warming bowl of claim 3, wherein said at least one light emitting device is a light emitting diode.

5. The irrigation liquid warming bowl according to claim 1, wherein said power supply means further comprises electric power connecting means for selectively optionally connecting said electrical circuitry to an electrical power source that is externally disposed in relation to said bowl assembly.

6. The irrigation liquid warming bowl of claim 5, wherein said electric power connecting means includes transforming from an external power source to a voltage that is isolated therefrom and that is low enough to avoid dangers of electrical shock upon accidental exposure thereto and that is compatible with the requirements of said heating means.

7. The irrigation liquid warming bowl of claim 5, wherein said power connecting means comprises:

a plug receptacle disposed partially in an outer surface of said outer bowl; and a supply connection device, said supply connection device including a connector/coupler, said connector/coupler being operative for coupling and connecting with said receptacle, said connector/coupler being operative in disconnecting said at least one battery from said electrical circuitry upon and while being coupled with said plug receptacle and connecting said supply connection device to said electrical circuitry instead.

8. The irrigation liquid warming bowl of claim 7, wherein said supply connection device further includes a power cord connected at one end thereof with said connector/coupler, and a supply plug unit connected with the other end of said power cord, said supply plug unit serving for plugging into an electrical power source that is externally disposed in relation to said bowl assembly.

9. A method for providing irrigation liquid substantially at body temperature during medical surgical procedures for application to body tissues, said method comprising the steps of:

(a) providing a warming bowl assembly comprising an inner bowl and an outer bowl and an internal region defined therebetween, said internal region being liquid-tightly sealed with respect to ambient and with respect to liquid held in said inner bowl, said inner bowl including a housing made of a non-metallic low-thermal-conductivity material fixedly supported substantially horizontally spacedly from the bottom of said inner bowl; said housing including therein an electrical heater and a preset thermostat, said heater being spaced in substantial thermal isolation within said housing from said preset thermostat, said housing further including a thermal shunt conductor disposed along at least a portion of the external periphery of said housing and extending laterally between vicinities of said heater and of said preset thermostat over and across the space therebetween, said thermal shunt conductor extending substantially over and about the vicinal area of said heater and substantially over and about the vicinal area of said preset thermostat so that the thermostat is exposed to and senses substantially primarily the temperature of the shunt conductor;

(b) filling said warming bowl assembly with irrigation liquid;

(c) providing an electrical power source supplying electrical power from the power source to said electrical heater via said thermostat by actuating a manual switch and thereby connecting said power source with said heater, said manual switch being located in part on the exterior of the warming bowl assembly, said power source including at least one battery that is held and sealed within said internal region;

(d) transferring heat from said heater through the wall of said housing to said thermal shunt conductor;

(e) conducting a portion of the heat transferred to said thermal shunt conductor therefrom by thermal conduction and convection via the surface area of said thermal shunt conductor that contacts irrigation liquid held in said inner bowl to the irrigation liquid and thereby heating the irrigation liquid;

(f) shunting another portion of the heat transferred to said thermal shunt conductor therefrom through the wall of said housing to said preset thermostat, said preset thermostat being operative in response to the temperature of said thermal shunt conductor;

(g) attaining a temperature in and at said thermal shunt conductor that is a function of the temperature of irrigation liquid contacted thereby and substantially corresponds thereto while irrigation liquid contacts a substantial part of the surface area of said thermal shunt conductor;

(h) reaching a temperature in and at said thermal shunt conductor that substantially corresponds to the cut-off temperature to which said thermostat is preset;

(i) attaining a temperature momentarily in and at said thermal shunt conductor that exceeds the cut-off temperature to which said thermostat is preset in response to absence of irrigation liquid in contact with at least a substantial part of the surface area of said thermal shunt conductor;

(j) switching off the supply of power to the heater by means of said preset thermostat in response to the temperature of said thermal shunt conductor exceeding the cut-off temperature to which said thermostat is preset;

(k) switching on the supply of power to the heater by means of said preset thermostat in response to the temperature of said thermal shunt conductor decreasing below the threshold temperature to which said thermostat is preset;

(l) visually displaying electrical operating status of said warming bowl assembly; and (m) removing irrigation liquid from said warming bowl assembly and applying irrigation liquid to bodily tissue for irrigation and lavage thereof.

10. The method according to claim 9, said power source further including an external power supply, said external power supply being disposed externally in relation to said warming bowl assembly, and wherein step (c) includes a step of selectively optionally interconnecting said electrical heater with said external power supply while substantially simultaneously disconnecting said at least one battery.

11. The method according to claim 9, further comprising the step of visually displaying by thermometric indicator means the temperature of liquid held in said warming bowl assembly.

12. The method according to claim 9, wherein step (l) includes visually displaying electrical operating status of steps (c), (j), and (k).

13. The method according to claim 9, wherein step (l) includes visually displaying by means of at least one light emitting diode the electrical operating status.

* * * * *